US012734219B2

(12) United States Patent
Chang et al.

(10) Patent No.: US 12,734,219 B2
(45) Date of Patent: Sep. 15, 2026

(54) SUSTAINED RELEASE FORMULATION COMPOSITION COMPRISING SEMAGLUTIDE OR PHARMACEUTICALLY ACCEPTABLE SALT THEREOF

(71) Applicant: PEPTRON, INC., Daejeon (KR)

(72) Inventors: Seung Gu Chang, Daejeon (KR); Jae Pyoung Cho, Chungcheongbuk-do (KR); Ji Hyang Lee, Chungcheongbuk-do (KR); Eun Seo Jang, Daejeon (KR); Ho Il Choi, Daejeon (KR)

(73) Assignee: Peptron, inc., Daejeon (KR)

( * ) Notice: Subject to any disclaimer, the term of this patent is extended or adjusted under 35 U.S.C. 154(b) by 429 days.

(21) Appl. No.: 18/565,190

(22) PCT Filed: Jun. 23, 2022

(86) PCT No.: PCT/KR2022/008984
§ 371 (c)(1),
(2) Date: Nov. 29, 2023

(87) PCT Pub. No.: WO2022/270956
PCT Pub. Date: Dec. 29, 2022

(65) Prior Publication Data

US 2024/0307500 A1 Sep. 19, 2024

Related U.S. Application Data

(60) Provisional application No. 63/213,805, filed on Jun. 23, 2021.

(30) Foreign Application Priority Data

Jun. 23, 2022 (KR) ........................ 10-2022-0077146

(51) Int. Cl.
*A61K 38/00* (2006.01)
*A61K 9/16* (2006.01)
*A61K 38/26* (2006.01)
*A61P 3/10* (2006.01)

(52) U.S. Cl.
CPC ............ *A61K 38/26* (2013.01); *A61K 9/1647* (2013.01); *A61K 9/1694* (2013.01); *A61P 3/10* (2018.01)

(58) Field of Classification Search
CPC .... A61K 38/26; A61K 9/1647; A61K 9/1694; A61P 3/10; A61P 3/04; A61P 1/16; A61P 25/28
See application file for complete search history.

(56) References Cited

FOREIGN PATENT DOCUMENTS

| | | | |
|---|---|---|---|
| JP | 2021-183718 | A | 12/2021 |
| KR | 10-2019-0064509 | A | 6/2019 |
| KR | 10-2019-0125940 | A | 11/2019 |
| KR | 10-2137786 | B1 | 7/2020 |
| KR | 10-2020-0135922 | A | 12/2020 |
| KR | 10-2021-0005700 | A | 1/2021 |
| KR | 10-2021-0014086 | A | 2/2021 |

OTHER PUBLICATIONS

International Search Report for PCT/KR2022/008984 mailed on Sep. 30, 2022.

Miaad Bader et al.,"Pharmacokinetics and efficacy of PT302, a sustained-release Exenatide formulation, in a murine model of mild traumatic brain injury", Neurobiology of Disease, Apr. 2019, vol. 124, pp. 439-453, https://doi.org/10.1016/j.nbd.2018.11.023 (English translation of Abstract is submitted herewith.).

Yazhou Li et al., "Pharmacokinetics of Exenatide in nonhuman primates following its administration in the form of sustained-release PT320 and Bydureon", Scientific Reports, 9, Article No. 17208 (2019) https://doi.org/10.1038/s41598-019-53356-2.

*Primary Examiner* — Jeanette M Lieb

(74) *Attorney, Agent, or Firm* — Wood, Phillips, Katz, Clark & Mortimer

(57) ABSTRACT

The present invention relates to sustained-release microspheres which include semaglutide or a pharmaceutically acceptable salt thereof, and a sustained-release formulation composition including the same, which enable long-term sustained release of a drug without an initial burst, and have no release delay (lag phase) while having excellent bioavailability.

15 Claims, 9 Drawing Sheets

Specification includes a Sequence Listing.

SUSTAINED RELEASE FORMULATION COMPOSITION COMPRISING SEMAGLUTIDE OR PHARMACEUTICALLY ACCEPTABLE SALT THEREOF

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2022/008984 filed on Jun. 23, 2022, which claims priority to the benefit of U.S. Application No. 63/213,805 filed on Jun. 23, 2021 and Korean Patent Application No. 10-2022-0077146 filed in the Korean Intellectual Property Office on Jun. 23 2022, the entire contents of which are incorporated herein by reference.

BACKGROUND

1. Technical Field

The present invention relates to a sustained-release formulation composition.

2. Background Art

Glucagon-like peptide receptor agonists (GLP-1 RAs) are a group of drugs used to treat type 2 diabetes and are very effective in lowering blood sugar levels. Compared to older insulin secretagogues such as sulfonylureas or meglitinides, GLP-1 RAs have an advantage of lower risk of causing hypoglycemia, but have a disadvantage of shorter period of action.

Treatment of chronic diseases such as type 2 diabetes requires long-term administration, such that long-acting drugs capable of reducing the patient's burden are preferred, and drugs with a longer administration interval tend to be used more. Byetta, the first GLP-1 RA drug, was developed as a twice-a-day injection preparation, followed by development of a once-a-day injection preparation, thus leading the market. Recently, once-a-week injection products occupy most of the market.

Thanks to the great success and spread of GLP-1 RA drugs, the demand for once-a-month or more medicines with a longer duration of drug effects is increasing, and the development thereof is also required. However, due to technical limitations, a long-acting drug with a longer administration interval than once-a-week has yet to be realized.

Meanwhile, sustained-release formulations using biodegradable polymers are being developed to implement long-term sustained release effects, but in the case of these formulations, biodegradable polymers with slow drug release are used to prolong the drug release duration and prevent an initial burst. As a result, there are problems in that, after administration, the drug does not come out for a considerable period of time (2-3 weeks at the shortest, and 1 month or more at the longest), or the cumulative release rate of the drug is 30% or less.

SUMMARY

An object of the present invention is to provide a sustained-release formulation including sustained-release microspheres which enable long-term sustained release of a drug without an initial burst, and have no release delay (lag phase) while having excellent bioavailability.

Another object of the present invention is to provide a method for production of a sustained-release formulation composition including sustained-release microspheres which enable long-term sustained release of a drug without an initial burst, and have no lag phase while having excellent bioavailability.

1. A sustained-release formulation composition, including: sustained-release microspheres which include semaglutide or a pharmaceutically acceptable salt thereof, and poly(lactide-co-glycolide);

wherein the semaglutide or the pharmaceutically acceptable salt thereof is included in an amount of 3% by weight or more and less than 9% by weight of the sustained-release microspheres, and wherein the poly(lactide-co-glycolide) is a mixture of low-viscosity PLGA having an intrinsic viscosity of 0.14 to 0.24 dL/g and high-viscosity PLGA having an intrinsic viscosity of 0.32 to 0.44 dL/g.

2. The sustained-release formulation composition according to the above 1, wherein a weight ratio of the low-viscosity PLGA and the high-viscosity PLGA in the mixture is 1:0.2 to 5.

3. The sustained-release formulation composition according to the above 1, wherein a molar ratio of lactide to glycolide in the high-viscosity PLGA is 50:45 to 55.

4. The sustained-release formulation composition according to the above 1, wherein the sustained-release microspheres are prepared by dissolving the semaglutide or the pharmaceutically acceptable salt thereof and the poly(lactide-co-glycolide) in glacial acetic acid and spraying the same using an ultrasonic spray nozzle, followed by volatilizing the solvent using dry air.

5. The sustained-release formulation composition according to the above 4, wherein the ultrasonic spray nozzle has a frequency of 60 kHz.

6. The sustained-release formulation composition according to the above 1, wherein less than 5% of the semaglutide is released within 24 hours after administration to SD rats, and 30% or more is released within 2 weeks, or 60% or more is released within 4 weeks.

7. The sustained-release formulation composition according to the above 1, wherein the composition is administered to a subject at an interval of 1 to 3 months.

8. The sustained-release formulation composition according to the above 1, wherein the poly(lactide-co-glycolide) is 91 to 97% by weight of the sustained-release microspheres.
9. The sustained-release formulation composition according to the above 1, wherein the sustained-release microspheres have an average particle size of 15 to 25 μm.
10. The sustained-release formulation composition according to the above 1, wherein the composition is used for treatment of diabetes, obesity, non-alcoholic steatohepatitis or degenerative brain disease.
11. The sustained-release formulation composition according to the above 10, wherein the degenerative brain disease is any one selected from the group consisting of Parkinson's disease, Alzheimer's disease, Huntington's disease, Lou Gehrig's disease, Creutzfeldt-Jakob disease, stroke, and multiple sclerosis.
12. A method for production of a sustained-release formulation composition, the method including: preparing a mixed solution by dissolving semaglutide or a pharmaceutically acceptable salt thereof and poly(lactide-co-glycolide) in an organic solvent; and drying the mixed solution to obtain microspheres, wherein the poly(lactide-co-glycolide) is a mixture of low-viscosity PLGA having an intrinsic viscosity of 0.14 to 0.24 dL/g and high-viscosity PLGA having an intrinsic viscosity of 0.32 to 0.44 dL/g.

13. The method according to the above 12, wherein a weight ratio of the low-viscosity PLGA and the high-viscosity PLGA in the mixture is 1:0.2 to 5.
14. The method according to the above 12, wherein a molar ratio of lactide to glycolide in the high-viscosity PLGA is 50:45 to 55.
15. The method according to the above 12, wherein the drying of the mixed solution is performed by a spray drying process.
16. A method for treating diabetes, obesity, non-alcoholic steatohepatitis or degenerative brain disease, including administering the sustained-release formulation composition according to any one of the above 1 to 10 to a subject.

The sustained-release formulation composition of the present invention enables long-term sustained release of a drug without an initial burst. Further, there is no release delay phenomenon while having excellent bioavailability.

The sustained-release formulation composition of the present invention may be administered to a subject at an interval of 1 month or more.

DETAILED DESCRIPTION

Figure 1:
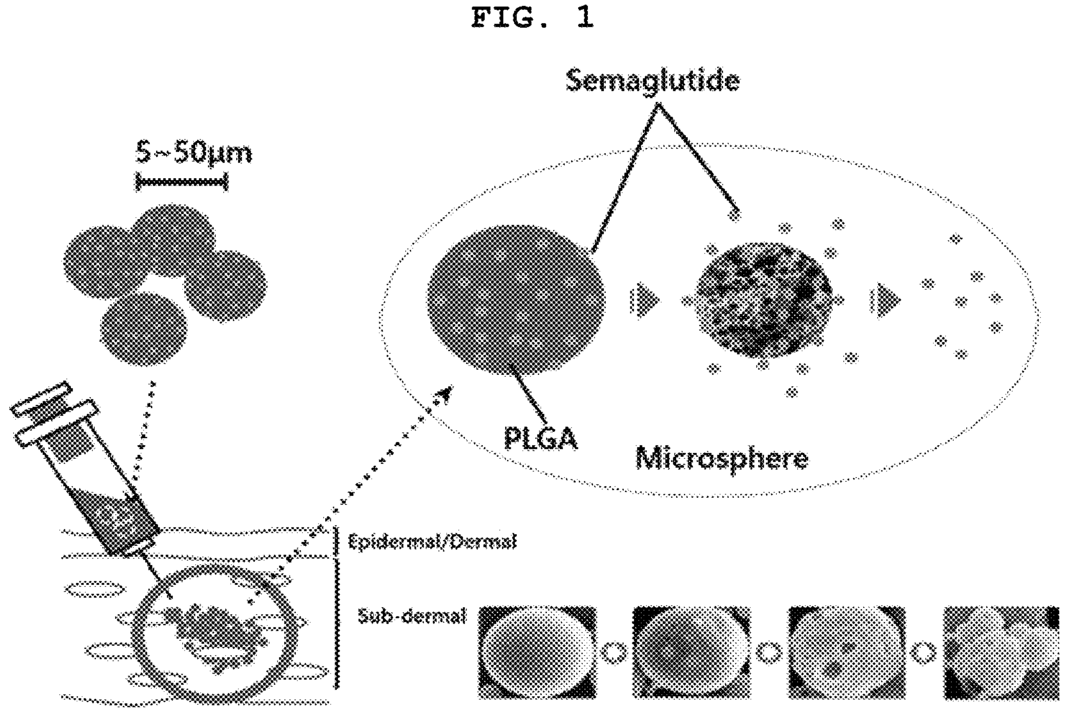
FIG. 1 is a schematic diagram briefly illustrating the release of semaglutide after subcutaneous injection of sustained-release microspheres of the present invention.

The present invention relates to sustained-release microspheres including semaglutide or a pharmaceutically acceptable salt thereof, which enable long-term sustained release of a drug without an initial burst, and have no lag phase while having excellent bioavailability, as well as a composition including the same.

The present invention provides a sustained-release formulation composition, including sustained-release microspheres which include semaglutide or a pharmaceutically acceptable salt thereof, and poly(lactide-co-glycolide).

Semaglutide is a GLP-1 receptor agonist that may be prepared as described in WO2006/097537, Example 4, and is also known as $N^{6,26}$-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid), 34-L-arginine] human glucagon-like peptide 1 (7-37).

A structure of semaglutide is represented by Formula 1 below.

[Formula 1]

(SEQ ID NO: 1)

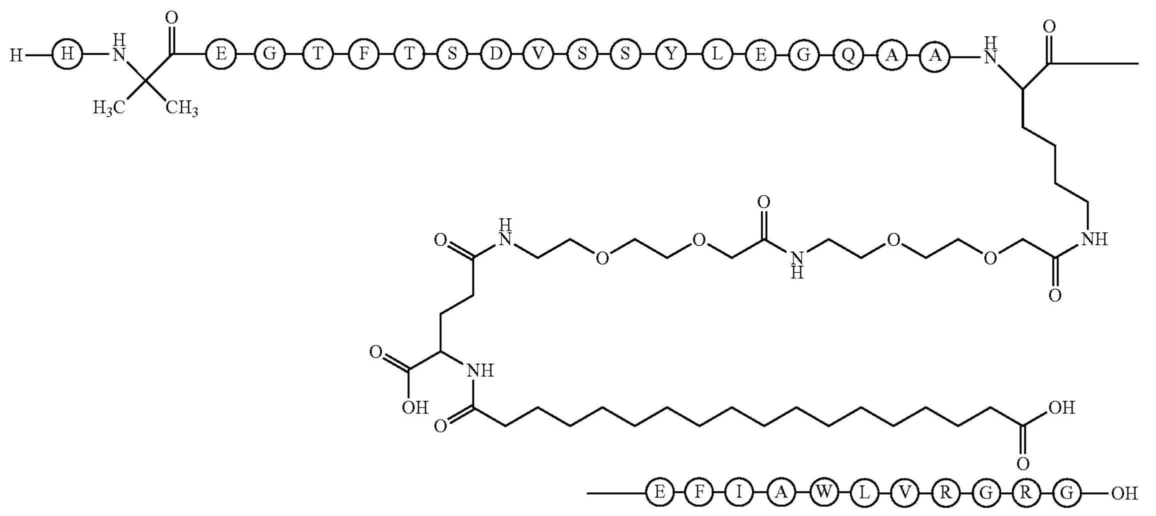

"The pharmaceutically acceptable salt" used herein refers to any salt having a concentration for effective action that is relatively non-toxic and harmless to patients, which does not reduce the beneficial efficacy of semaglutide due to side effects caused by the salt, and may be an acid addition salt or base addition salt. Among the pharmaceutically acceptable salts of semaglutide, the acid addition salt may include, for example, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, genticinate, fumarate, gluconate, glucuronate, saccharate, formate, benzoate, glutamate, methanesulfonate, ethanesulfonate, benzenesulfonate, p-toluenesulfonate, butyrate, camphorate, camphorsulfonate, digluconate, glycerophosphate, hemisulfate, heptanoate, hexanoate, 2-hydroxyethanesulfonate (isethionate), nicotinate, 2-naphthalenesulfonate, oxalate, pectinate, persulfate, 3-phenylpropionate, picrate, pivalate, propionate, thiocyanate, or bicarbonate of semaglutide.

Among the pharmaceutically acceptable salts of semaglutide, the base addition salt may include, for example, alkali metal salts, alkaline earth metal salts or quaternary ammonium salts of semaglutide.

The sustained-release microspheres including the semaglutide or the pharmaceutically acceptable salt thereof; and poly(lactide-co-glycolide) of the present invention may have a weight in the range of 20 to 6000 mg, 20 to 4000 mg, 100 to 6000 mg, 100 to 4000 mg, 500 to 6000 mg, 500 to 4000 mg, 1000 to 6000 mg, 1000 to 4000 mg, 1500 to 6000 mg, 1500 to 4000 mg, 2000 to 6000 mg, 2000 to 4000 mg, 2400 to 6000 mg, 2400 to 4000 mg, or 2400 to 3600 mg.

The semaglutide or the pharmaceutically acceptable salt thereof contained in the sustained-release microspheres of the present invention may be less than 9 wt. % based on a total weight of the sustained-release microspheres, preferably 3 wt. % or more and less than 9 wt. %, or 3 wt. % or more and 8.8 wt. % or less, 3 wt. % or more and 8.5 wt. % or less, 3 wt. % or more and 8.2 wt. % or less, 3 wt. % or more and 8 wt. % or less, or 3 wt. % or more and 6 wt. % or less. When the content of the semaglutide or the pharmaceutically acceptable salt thereof is 3 wt. % or more and 10 wt. % or less, the bioavailability is excellent. However, when the content of the semaglutide or the pharmaceutically acceptable salt thereof is 9 wt. % or more, the initial release rate is rapidly increased. Thus, the semaglutide or the pharmaceutically acceptable salt thereof is preferably included in an amount of 3 wt. % or more and less than 9 wt. % based on the total weight of the sustained-release microspheres.

Poly(lactide-co-glycolide) (PLGA) included in the sustained-release microspheres of the present invention may be a mixture of a low-viscosity PLGA having an intrinsic viscosity of 0.14 to 0.24 dL/g and a high-viscosity PLGA having an intrinsic viscosity of 0.32 to 0.44 dL/g. In the mixture of the low-viscosity PLGA and the high-viscosity PLGA, a weight ratio of low-viscosity PLGA having an intrinsic viscosity of 0.14 to 0.24 dL/g and high-viscosity PLGA having an intrinsic viscosity of 0.32 to 0.44 dL/g may be 1:0.2 to 5, 1:0.2 to 3, 1:0.3 to 5, 1:0.3 to 3, 1:0.5 to 5, 1:0.5 to 3, 1:0.5 to 2, 1:1 to 5, 1:1 to 3, 1:1 to 2.5, 1:1.5 to 2.5 or 1:1.8 to 2.2, and preferably 1:1.8 to 2.2.

If the poly(lactide-co-glycolide) included in the sustained-release microspheres consists of only the low-viscosity PLGA, the initial release amount of semaglutide becomes too large, and if it consists of only the high-viscosity PLGA, there is a problem in that the initial release amount of semaglutide is small, but the lag phase may occur and the overall release amount is reduced to deteriorate the bioavailability.

The sustained-release microspheres of the present invention may include a poly(lactide-co-glycolide) mixture in which the low-viscosity PLGA having an intrinsic viscosity of 0.14 to 0.24 dL/g and the high-viscosity PLGA having an intrinsic viscosity of 0.32 to 0.44 dL/g are mixed, preferably the low-viscosity PLGA and the high-viscosity PLGA are mixed in a weight ratio of 1:0.2 to 5, and more preferably the low-viscosity PLGA and the high-viscosity PLGA are mixed in a weight ratio of 1:1.8 to 2.2, such that the initial burst of semaglutide does not occur, while having no lag phase but excellent bioavailability.

The intrinsic viscosity (IV) of the poly(lactide-co-glycolide) (PLGA) of the present invention is a viscosity measured using an Ubbelohde viscometer at 25° C. after dissolving the same in chloroform at a concentration of 0.1% (W/V).

A molar ratio of lactide to glycolide in the low-viscosity PLGA having an intrinsic viscosity of 0.14 to 0.24 dL/g may be 80 to 45:50, 80 to 70:50, 75 to 50:50, 70 to 45:50, 65 to 50:50 or 55 to 45:50, and preferably 55 to 45:50. Among commercially available materials, examples of the low-viscosity PLGA having an intrinsic viscosity of 0.14 to 0.24 dL/g may include RG502, RG502H, RG752H and RG752S available from Evonik.

A molar ratio of lactide to glycolide in the high-viscosity PLGA having an intrinsic viscosity of 0.32 to 0.44 dL/g may be 80 to 45:50, 75 to 50:50, 70 to 45:50, 65 to 50:50 or 55 to 45:50, and preferably 55 to 45:50. Among commercially available materials, examples of the high-viscosity PLGA having an intrinsic viscosity of 0.32 to 0.44 dL/g may include RG503, RG503H, RG653H, RG752H and RG753S available from Evonik.

The mixture of poly(lactide-co-glycolide) mixed with the low-viscosity PLGA having an intrinsic viscosity of 0.14 to 0.24 dL/g and the high-viscosity PLGA having an intrinsic viscosity of 0.32 to 0.44 dL/g included in the sustained-release microspheres of the present invention may be included in an amount of 80 wt. % or more or 90 wt. % or more based on the total weight of the microspheres, and more specifically 90 to 99 wt. %, 90 to 97 wt. %, 90 to 96 wt. %, 91 to 99 wt. %, 91 to 97 wt. %, 91 to 96 wt. %, 92 to 99 wt. %, 92 to 97 wt. %, 92 to 96 wt. %, 93 to 99 wt. %, 93 to 97 wt. %, 93 to 96 wt. %, 94 to 99 wt. %, 94 to 97 wt. % or 94 to 96 wt. %.

The sustained-release microspheres of the present invention may include, for example, 3 wt. % or more and less than 9 wt. % of semaglutide or a pharmaceutically acceptable salt thereof, and 90 to 97 wt. % or 91 to 97 wt. % of poly (lactide-co-glycolide), in addition, additional coating materials, additives, or excipients may be further included.

After the sustained-release formulation composition containing the sustained-release microspheres of the present invention is administered to Sprague Dawley rats (SD rats), the semaglutide may be released at 5% or less within 24 hours, and further, at 30% or more within 2 weeks, or 60% or more within 4 weeks.

Figure 6:
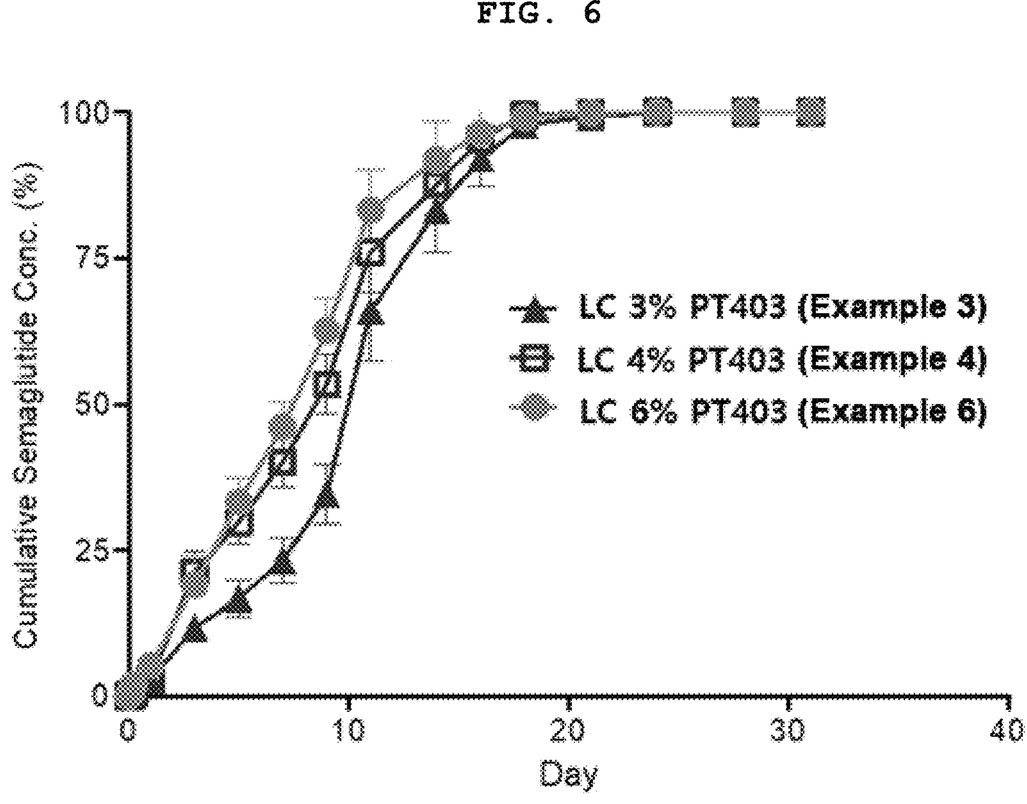
FIG. 6 illustrates semaglutide cumulative release rates over time after administration of the formulations in Examples 3, 4 and 6, having semaglutide contents (Loading Capacity, LC) of 3, 4 and 6 wt. %, respectively, at the same dose of 4 mpk to male 8-week-old SD rats.
Figure 8:
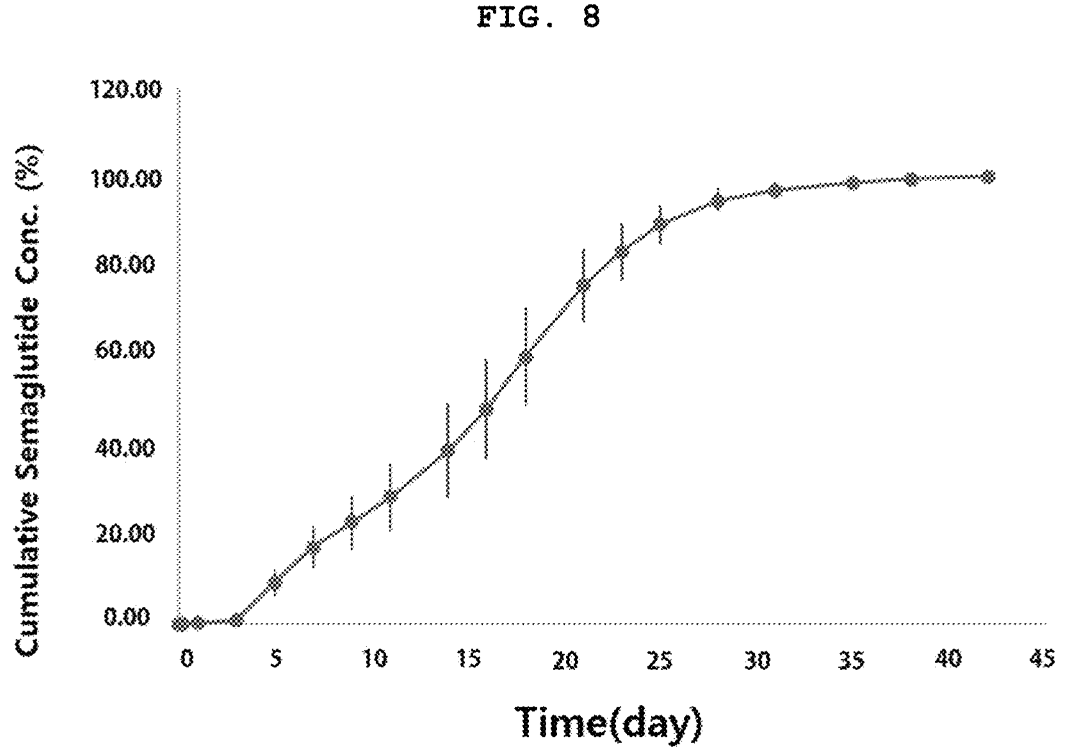
FIG. 8 illustrates semaglutide cumulative release rates over time after administration of the formulation in Example 3 at a dose of 4 mpk to a male Beagle.

In one embodiment of the present invention, after administering the sustained-release microspheres of the present invention to SD rats, it was confirmed that the semaglutide was released at 5% or less within 24 hours, 30% or more within 2 weeks, and 60% or more within 4 weeks (FIG. 6 and Table 7). Further, it was confirmed that the semaglutide was released at 5% or less within 24 hours in Beagle dogs, 30% or more within 2 weeks, and 60% or more within 4 weeks (FIG. 8 and Table 8).

The sustained-release microspheres of the present invention may be coated with lysine, and the lysine applied to the sustained-release microspheres may be included in an amount of 0.01 to 5, 0.01 to 3, 0.01 to 1, or 0.1 to 1 parts by weight ("wt. parts"), and preferably 0.2 to 0.8 or 0.4 to 0.6 wt. parts based on 100 wt. parts of the sustained-release microspheres before coating.

The sustained-release formulation composition including the sustained-release microspheres of the present invention may maintain effects for 3 weeks or 1 month or more with a single administration depending on the subject the sustained-release to be administered, therefore, formulation composition of the present invention may be administered at an interval of 1 month to 2 months, 1 month to 1.5 months, or 1 month.

In one embodiment of the present invention, it was confirmed that the semaglutide was continuously released for 3 weeks or more (T last=35 days) after administration of the sustained-release microspheres E the present invention to rats. Further, it was confirmed that, after administration to Beagle dogs, the semaglutide was continuously released for 4 weeks or more (T last=63 days). In general, according to the animal species as the subjects to be administered, it is known that the larger the species, the longer the time of absorption, distribution, metabolism, etc. of the drug, and the longer the release and duration of the drug (allometric scaling). Accordingly, in one embodiment, it was also confirmed that the duration of drug effects of semaglutide was longer in Beagles than in rats. For the same reason, when administered to a person with a larger object size, the duration of drug effects is longer than when administered to a Beagle. Therefore, when administered to humans, the drug effects may last for 1 month or more with one administration, and more specifically, the drug effects may last for 1 month to 3 months, 1 month to 2 months, or 1 month to 1.5 months.

The sustained-release microspheres of the present invention may have an average particle size of 5 to 50 μm, 5 to 40 μm, 5 to 30 μm, 10 to 50 μm, 10 to 40 μm, 10 to 30 μm, 10 to 25 μm, 15 to 50 μm, 15 to 40 μm, and 15 to 30 μm, or 15 to 25 μm. As used herein, the "average particle size (D50)" means a particle size corresponding to 50% of the volume % in the particle size distribution curve.

A span value of the sustained-release microspheres of the present invention is 2 or less, and more specifically, the span value may be 0.1 to 2, 0.1 to 1.8, 0.3 to 2, 0.3 to 1.8, 0.5 to 2, 0.5 to 1.8, 0.8 to 2, 0.8 to 1.8, 1 to 2, 1 to 1.8, or 1 to 1.6.

The sustained-release microspheres or the sustained-release formulation composition including the same of the present invention may further include additives and excipients commonly used in the formulation of drugs in the art, to which the present invention pertains.

The sustained-release microspheres of the present invention may further include at least one protective colloid selected from the group consisting of polyvinyl alcohol, albumin, polyvinylpyrrolidone, gelatin and the like. The protective colloidal material serves to prevent aggregation between microspheres including semaglutide and improve dispersibility. The content of the protective colloid is preferably 0.02 to 1.0 wt. % based on the total weight of the sustained-release microspheres.

The sustained-release formulation composition including the sustained-release microspheres according to the present invention may be used to treat diabetes, obesity, non-alcoholic steatohepatitis (NASH) or degenerative brain disease.

The degenerative brain disease may be any one selected from the group consisting of Parkinson's disease, Alzheimer's disease, Huntington's disease, Lou Gehrig's disease, Creutzfeldt-Jakob disease, stroke, and multiple sclerosis.

The sustained-release microspheres of the present invention may be prepared by dissolving the semaglutide or the pharmaceutically acceptable salt thereof and the poly(lactide-co-glycolide) in glacial acetic acid, spraying the same through an ultrasonic spray nozzle, and then volatilizing the solvent using dry air.

The present invention provides a method for production of sustained-release microspheres which enable long-term sustained release of a drug without an initial burst, and have no lag phase while having excellent bioavailability.

The method for production of sustained-release formulation composition of the present invention may include: preparing a mixed solution by dissolving semaglutide or a pharmaceutically acceptable salt thereof and poly(lactide-co-glycolide) in an organic solvent; and drying the mixed solution to obtain microspheres.

In the method for production of the sustained-release formulation composition of the present invention, the type of poly(lactide-co-glycolide) dissolved together with the semaglutide or the pharmaceutically acceptable salt thereof may be substantially the same as described above for the sustained-release microspheres of the present invention.

With regard to the method for production of sustained-release formulation composition of the present invention, a weight ratio of the semaglutide and the poly(lactide-co-glycolide dissolved in the organic solvent may be appropriately adjusted so that a content of semaglutide in the prepared sustained-release microspheres becomes less than 9 wt. %, and preferably 3 wt. % or more and less than 9 wt. %, 3 wt. % or more and 8.8 wt. % or less, 3 wt. % or more and 8.5 wt. % or less, 3 wt. % or more and 8.2 wt. % or less, 3 wt. % or more 8 wt. % or less, or 3 wt. % or more and 6 wt. % or less.

The organic solvent may be one selected from the group consisting of chloroform, ethyl acetate, methylene chloride, methyl ethyl ketone, alcohol having 1 to 5 carbon atoms, glacial acetic acid, formic acid, dimethylsulfoxide, and n-methylpyrrolidone or a mixed solvent thereof, and preferably glacial acetic acid.

With regard to the method for production of the sustained-release formulation composition of the present invention, a spray drying process may be used as a method of obtaining microspheres by drying the mixed solution.

The spray drying process may be executed by supplying the mixed solution in which the semaglutide or the pharmaceutically acceptable salt thereof, and the poly(lactide-co-glycolide) are dissolved, to a spray dryer at a flow rate of 5 to 20 mL/min, 5 to 15 mL/min or 5 to 10 mL/min, and then feeding dry air at 100 to 200° C., 100 to 150° C. or 120 to 150° C. Further, the spray dryer may have a frequency of 40 to 80 kHz, 50 to 70 kHz or 55 to 75 kHz, and preferably 60 KHz.

The method for production of the formulation composition of the present invention may further include lysine coating by suspending the dried microspheres in an aqueous solution containing lysine hydrochloride dissolved therein, after the step of drying the mixed solution to obtain microspheres.

A concentration of the lysine hydrochloride in the aqueous solution containing lysine hydrochloride dissolved therein may be 0.01 M to 1 M, and preferably 0.1 M to 0.6 M. When the concentration of lysine hydrochloride is lower than 0.01 M, the surface of the microspheres cannot be sufficiently coated with lysine. On the other hand, when the concentration is higher than 1 M, the lysine hydrochloride is supersaturated, which is inefficient.

Further, the aqueous solution containing lysine hydrochloride dissolved therein may further include 1% (W/V) polyvinyl alcohol.

The present invention provides a method for treating diabetes, obesity, non-alcoholic steatohepatitis or degenerative brain disease, which includes: administering the sustained-release formulation composition including the sustained-release microspheres according to the present invention to a subject.

The degenerative brain disease may be any one selected from the group consisting of Parkinson's disease, Alzheimer's disease, Huntington's disease, Lou Gehrig's disease, Creutzfeldt-Jakob disease, stroke, and multiple sclerosis.

The sustained-release formulation composition including the sustained-release microspheres of the present invention may be administered via an oral or parenteral route, and preferably via a parenteral route such as intravenous administration, subcutaneous administration, intramuscular administration, or intraperitoneal administration.

An effective dosage of the sustained-release formulation composition according to the present invention may be appropriately adjusted based on an age of the patient, the type and severity of the disease, and the condition of the patient. For example, it may be 0.1 to 10 mg/week based on an amount of active ingredients. The dose may be administered at one time or administered in divided doses.

Hereinafter, the present invention will be described in more detail through examples.

Preparative Example: Preparation of Sustained-Release Microspheres and Particle Size of the Prepared Microspheres

1) Preparation of Sustained-Release Microspheres (Examples 1-6 and Comparative Examples 1-12)

Semaglutide as a GLP-1 receptor agonist, and prepare microspheres. The types of biodegradable polymers used for preparing the microspheres are shown in Table 1 below, and the compositions for preparing various microspheres containing semaglutide are shown in Table 2 below. For PLGA, Resomers commercially available from Evonik were used. As described in Table 1 below, PLGA75A, PLGA75B, PLGA65B, PLGA50A and PLGA50B represent the used RG752H, RG753H, RG653H, RG502H and RG503H, respectively, which are Resomers commercially available from Evonik.

TABLE 1

| Division | Polymer grade | Viscosity (dL/g) |
|---|---|---|
| 1 | Poly(D,L-lactide) (PLA) | 0.16-0.24 |
| 2 | Poly(D,L-lactide-co-glycolide) (75:25) (PLGA75A) | 0.14-0.22 |
| 3 | Poly(D,L-lactide-co-glycolide) (75:25)(PLGA75B) | 0.32-0.44 |
| 4 | Poly(D,L-lactide-co-glycolide) (65:35) (PLGA65) | 0.32-0.44 |
| 5 | Poly(D,L-lactide-co-glycolide) (50:50) (PLGA50A) | 0.16-0.24 |
| 6 | Poly(D,L-lactide-co-glycolide)(50:50) (PLGA50B) | 0.32-0.44 |

PLGA75A: RG752H/PLGA75B: RG753H/PLGA65B: RG653H/PLGA50A: RG502H/PLGA50B: RG503H/

The spray drying process was performed by feeding the prepared mixed solution at a flow rate of 7.5 mL/min to a spray dryer (EIN System) equipped with an ultrasonic nozzle (Sonictopia, 60 kHz) using a liquid peristaltic pump (Master flex), regulating a power of an oscillator (Sonictopia, 60 kHz) between 50 and 75% and supplying dry air at 135° C. The microspheres prepared through the spray drying process were dispersed in an aqueous solution containing 1% (W/V) polyvinyl alcohol (Mitsubishi Chemical Corporation) and 0.5M L-lysine hydrochloride (Merck) as a protective colloid, and then stirred for 3 hours. Thereafter, the microspheres were collected through filtration and washing with distilled water, suspended by adding 10% D-mannitol (ROQUETTE) and 0.5% L-lysine hydrochloride (Merck) solution thereto, followed by freeze-drying to obtain sustained-release microspheres of the present invention. Table 2 shows the types and mixing ratios of biodegradable polymers for each sustained-release microsphere formulation.

TABLE 2

| Division | Type of biodegradable polymers and mixing ratio | | | Drug |
|---|---|---|---|---|
| | Polymer type (1) | Polymer type (2) | (1):(2) mixing ratio | loading (%(w/w)) |
| Example 1 | PLGA50A | PLGA50B | 1:1 | 3 |
| Example 2 | PLGA50A | PLGA50B | 1:3 | 3 |
| Example 3 | PLGA50A | PLGA50B | 1:2 | 3 |
| Example 4 | PLGA50A | PLGA50B | 1:2 | 4 |
| Example 5 | PLGA50A | PLGA50B | 1:2 | 5 |
| Example 6 | PLGA50A | PLGA50B | 1:2 | 6 |
| Comparative Example 1 | PLGA50A | PLGA50B | 1:2 | 1 |
| Comparative Example 2 | PLGA50A | PLGA50B | 1:2 | 9 |
| Comparative Example 3 | PLGA50A | PLGA50B | 1:2 | 12 |
| Comparative Example 4 | PLGA50A | PLGA50B | 1:2 | 15 |
| Comparative Example 5 | PLA | — | 1:0 | 3 |
| Comparative Example 6 | PLGA75A | — | 1:0 | 3 |
| Comparative Example 7 | PLGA75B | — | 1:0 | 3 |
| Comparative Example 8 | PLGA65B | — | 1:0 | 3 |
| Comparative Example 9 | PLGA50A | — | 1:0 | 3 |
| Comparative Example 10 | PLGA50B | — | 1:0 | 3 |
| Comparative Example 11 | PLGA50A | PLGA75A | 1:1 | 3 |
| Comparative Example 12 | PLGA50A | PLA | 1:1 | 3 |

Table 3 shows amounts of biodegradable polymers (PLGA and PLA), drug (semaglutide) and solvent used for preparing sustained-release microspheres by the spray drying process.

TABLE 3

| Division | Amount of polymer used (mg) | Amount of drug used (mg) | Amount of solvent used (mL) |
|---|---|---|---|
| Example 1 | 2880.0 | 135.97 | 28.8 |
| Example 2 | 2880.0 | 135.97 | 28.8 |
| Example 3 | 3360.0 | 160.83 | 33.6 |
| Example 4 | 3314.5 | 213.1 | 33.2 |
| Example 5 | 3264.4 | 270.63 | 32.6 |
| Example 6 | 3220.0 | 321.66 | 32.2 |
| Comparative Example 1 | 5423.0 | 87.25 | 54.2 |
| Comparative Example 2 | 2643.0 | 404.51 | 26.4 |
| Comparative Example 3 | 2526.0 | 537.08 | 25.3 |
| Comparative Example 4 | 2409.0 | 669.65 | 24.1 |
| Comparative Example 5 | 2880.0 | 135.97 | 28.8 |

TABLE 3-continued

| Division | Amount of polymer used (mg) | Amount of drug used (mg) | Amount of solvent used (mL) |
|---|---|---|---|
| Comparative Example 6 | 2880.0 | 135.97 | 28.8 |
| Comparative Example 7 | 2880.0 | 135.97 | 28.8 |
| Comparative Example 8 | 2880.0 | 135.97 | 28.8 |
| Comparative Example 9 | 2880.0 | 135.97 | 28.8 |
| Comparative Example 10 | 2880.0 | 135.97 | 28.8 |
| Comparative Example 11 | 2880.0 | 135.97 | 28.8 |
| Comparative Example 12 | 2880.0 | 135.97 | 28.8 |

2) Measurement of Particle Size of Prepared Microspheres

An average particle size and distribution of the prepared microspheres were quantitatively measured. Specifically, 180 mg of the microspheres and 10 ml of 1% PVA were introduced in 50 ml conical tube, and then fed to an ultrasonic generator for 1 minute to disperse the same, followed by placing the product to a particle size analyzer (CILAS, French) to determine the particle sizes. As an indicator of particle size uniformity, a span value is calculated by Equation 1 below.

$$\text{Span Value} = (D\ 90 - D\ 10)/D\ 50 \qquad \text{[Equation 1]}$$

Table 4 shows the average particle size of the prepared microspheres and the span value.

TABLE 4

| Division | Average particle size of microspheres (μm) | Span value |
|---|---|---|
| Example 1 | 19.50 | 1.48 |
| Example 2 | 20.80 | 1.49 |
| Example 3 | 20.48 | 1.54 |
| Example 4 | 20.77 | 1.49 |
| Example 5 | 21.35 | 1.47 |
| Example 6 | 21.12 | 1.48 |
| Comparative Example 1 | 21.52 | 1.52 |
| Comparative Example 2 | 21.48 | 1.49 |
| Comparative Example 3 | 22.37 | 1.42 |
| Comparative Example 4 | 23.53 | 1.55 |
| Comparative Example 5 | 19.85 | 1.43 |
| Comparative Example 6 | 20.12 | 1.43 |
| Comparative Example 7 | 21.61 | 1.52 |
| Comparative Example 8 | 21.63 | 1.53 |

TABLE 4-continued

| Division | Average particle size of microspheres (μm) | Span value |
|---|---|---|
| Comparative Example 9 | 23.35 | 1.42 |
| Comparative Example 10 | 20.17 | 1.53 |
| Comparative Example 11 | 19.62 | 1.42 |
| Comparative Example 12 | 18.39 | 1.61 |

Experimental Example 1: Measurement of In Vitro Release of Microspheres

Microspheres containing 100 μg of semaglutide were suspended in a glass container in which 3 mL of release solution (0.5 PVA+0.1M phosphate buffer (pH 7.0)) is contained, and sealed to prevent leakage of water. Then, the container was placed in water preheated to 37° C., followed by rotating the same at a speed of 20 rpm. After a predetermined time has elapsed, a sample was collected and subjected to HPLC analysis. As a result, it was confirmed that the exhibited initial release rates were different depending on a drug loading capacity and the type and mixing ratio of biodegradable polymers.

Figure 2:
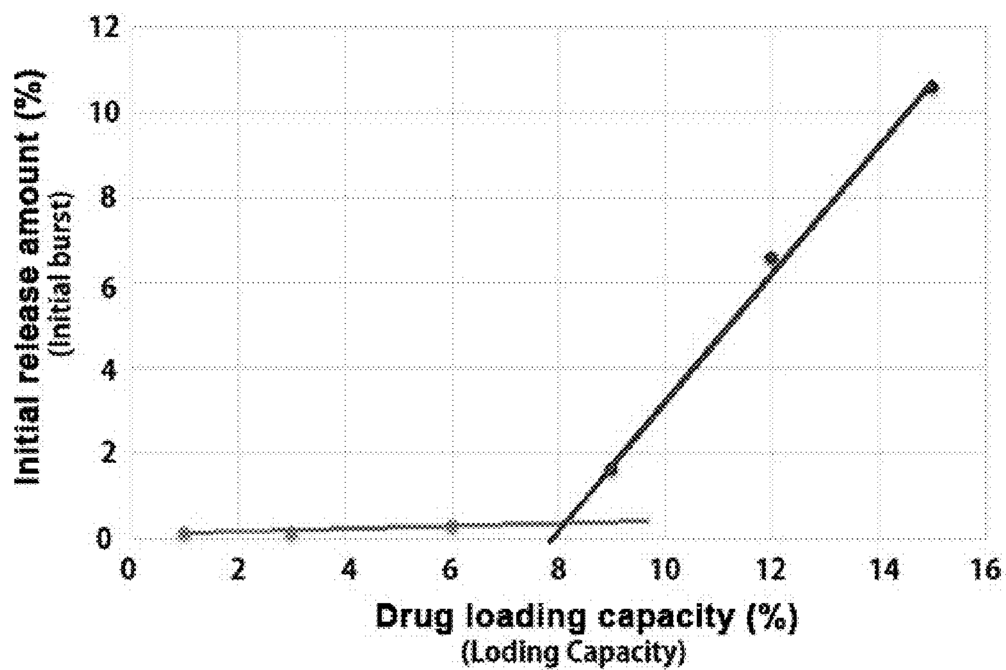
FIG. 2 illustrates in vitro initial release evaluation results (after 6 hours) of sustained-release microspheres of formulations in Examples 3 and 6 and Comparative Examples 1 to 4, respectively.

Generally, it was demonstrated that initial release was gradually increased as a drug content is higher, and when the drug content exceeds 9%, the initial release was rapidly increased (see FIG. 2). Accordingly, it could be determined that a maximum loading capacity of drug in the microspheres without rapid initial release is less than 9% (w/w).

Table 5 shows a change in the initial release to drug (semaglutide) loading capacity (in vitro release experiment, after lapse of 6 hours and 24 hours) below.

TABLE 5

| | Type of biodegradable polymers and mixing ratio | | | | | |
|---|---|---|---|---|---|---|
| | Low viscosity polymer (viscosity: 0.14- | High viscosity polymer (viscosity: 0.32- | | Drug | Initial release (%) | |
| Division | 0.24 dL/g | 0.44 dL/g) | Mixing ratio | loading (%(w/w)) | 6 hours | 1 day |
| Example 3 | PLGA50A | PLGA50B | 1:2 | 3 | 0.17 | 1.6 |
| Example 6 | PLGA50A | PLGA50B | 1:2 | 6 | 0.44 | 7.5 |
| Comparative Example 1 | PLGA50A | PLGA50B | 1:2 | 1 | 0.16 | 1.5 |
| Comparative Example 2 | PLGA50A | PLGA50B | 1:2 | 9 | 2.63 | 27.2 |
| Comparative Example 3 | PLGA50A | PLGA50B | 1:2 | 12 | 6.61 | 49.4 |
| Comparative Example 4 | PLGA50A | PLGA50B | 1:2 | 15 | 10.6 | 90.4 |

In the case of using only a low-viscosity polymer or using a mixture of two different low-viscosity polymers, it could be seen that the initial release was high (Comparative Examples 5, 6, 9, 11 and 12). On the other hand, when using the high-viscosity polymers, the initial release was low (Comparative Examples 7, 8 and 10). Further, when using a mixture of the high-viscosity polymer and the low-viscosity polymer, it could also be seen that the initial release was low (Examples 1, 2 and 3). Table 6 shows a change in the initial release to the type of polymers and mixing ratio thereof (in vitro release experiment, after the lapse of 24 hours).

TABLE 6

| | Type of biodegradable polymers and mixing ratio | | | | |
|---|---|---|---|---|---|
| Division | Low viscosity polymer (viscosity: 0.14-0.24 dL/g | High viscosity polymer (viscosity: 0.32-0.44 d L/g) | Mixing ratio | Drug loading (%(w/w)) | Initial release (%) 1 day |
| Example 1 | PLGA50A | PLGA50B | 1:1 | 3 | 2.8 |
| Example 2 | PLGA50A | PLGA50B | 1:3 | 3 | 2.6 |
| Example 3 | PLGA50A | PLGA50B | 1:2 | 3 | 1.6 |
| Example 5 | PLA | — | 1:0 | 3 | 17.5 |
| Comparative Example 6 | PLGA75A | — | 1:0 | 3 | 10.6 |
| Comparative Example 9 | PLGA50A | — | 1:0 | 3 | 6.5 |
| Comparative Example 7 | — | PLGA75B | 0:1 | 3 | 1.3 |
| Comparative Example 8 | — | PLGA65B | 0:1 | 3 | 1.2 |
| Comparative Example 10 | — | PLGA50B | 0:1 | 3 | 1.4 |
| Comparative Example 11 | PLGA50A + PLGA75A (1:1) | — | 1:0 | 3 | 10.5 |
| Comparative Example 12 | PLGA50A + PLA (1:1) | — | 1:0 | 3 | 101.4 |

As described in Table 6 above, in the case of microspheres composed of high-viscosity polymers, the initial release was low, but the lag phase became longer and the total release amount was low, thereby resulting in low bioavailability. As a result, there is i) no initial burst, ii) long-term sustained release is possible, iii) there is no lag phase, and iv) it is not suitable as a component of the sustained-release formulation with excellent bioavailability. On the other hand, in the case of the high-viscosity polymer and the low-viscosity polymer were mixed and used, it was confirmed that the initial burst could be prevented, and the PK profile in rats was investigated in order to determine whether the delayed release could be suppressed (see Experimental Example 3).

Experimental Example 2: Experiment on Blood Sugar Control and Weight Loss Effects of Sustained-Release Microspheres Including Semaglutide (In Vivo Experiment)

An oral glucose tolerance test (OGTT) was performed to confirm hypoglycemic effects of the sustained-release microspheres including semaglutide of the present invention. First, the experiment was conducted by dividing 8-week-old SD rats (18 rats; 6 rats in each group) into 3 groups. It was divided into a negative control group (Control), a positive control group (API) and Example 3 formulation administration group (PT403)), wherein the positive control group (API) was subcutaneously injected once with 0.123 mpk of semaglutide, and the Example 3 formulation administration group (PT403) was injected with the Example 3 formulation subcutaneously with 4 mpk.

After drug administration, total 5 OGTTs (Days 1, 7, 16, 21 and 28) were performed, and 2 g/kg of glucose was orally administered to SD rats fasted for 18 hours. Immediately after glucose administration, and after 15, 30, 60, 90, 120, and 180 minutes, blood was collected from the tail to measure blood glucose.

Figure 3:
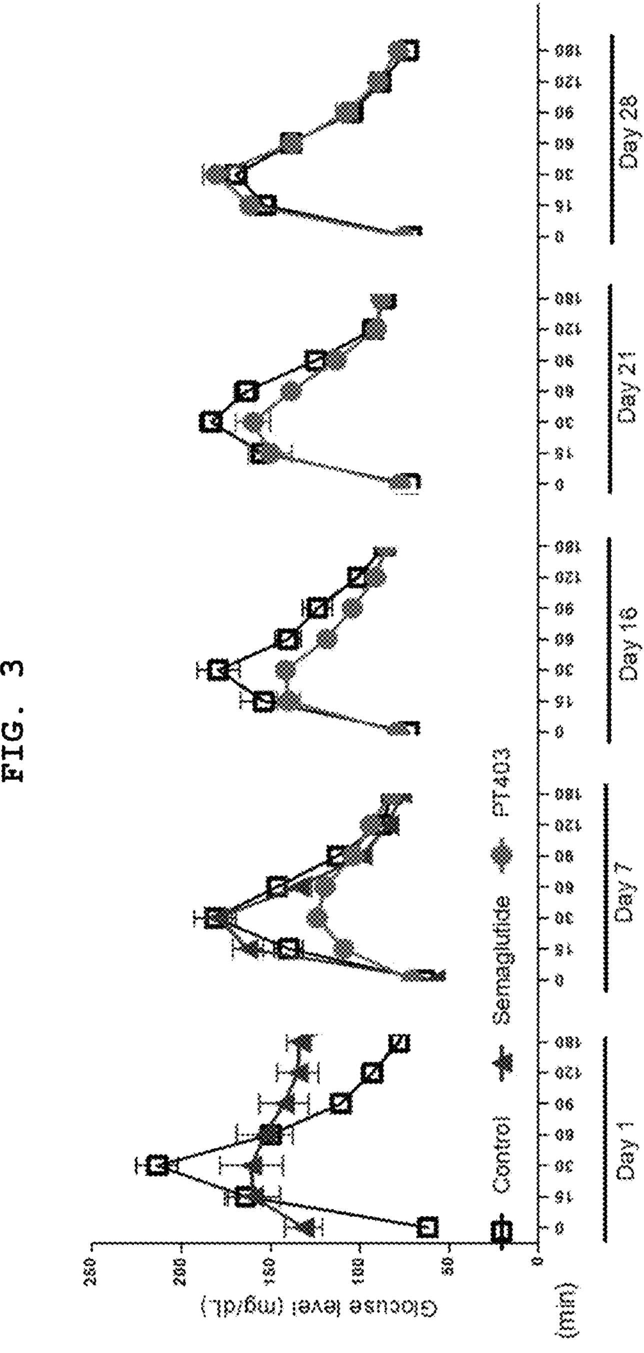
FIG. 3 illustrates linear time-dependent glucose lowering effects after subcutaneous injection of semaglutide and sustained-release microspheres (PT403) of a formulation in Example 3 in SD rats, wherein blood glucose levels were measured using Accu-Chek for 28 days after injection.
Figure 4:
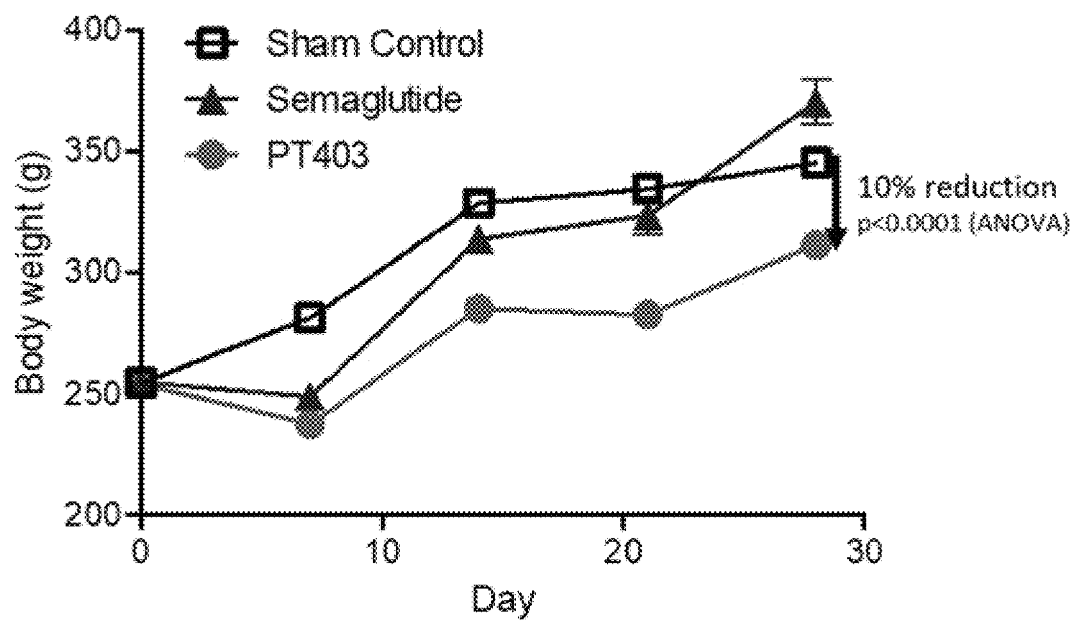
FIG. 4 illustrates a change in the body weight after subcutaneous injection of the semaglutide and sustained-release microspheres (PT403) of the formulation in Example 3 to SD rats.

As shown in FIG. 3, the group administered with the formulation of Example 3 (PT403) induced a decrease in the glucose level in a time-dependent manner, and in particular, hypoglycemic effects were maintained until about the $21^{st}$ day. On the other hand, the positive control group (API) had hypoglycemic effects on the $1^{st}$ day, but returned to normal on the $7^{th}$ day (FIG. 3). Further, in parallel with the OGTT analysis, the body weight of each rat was measured over time, and the Example 3 formulation administration group (PT403) showed a statistically significant weight loss of about 10% compared to the positive control group (API) as well as the negative control group (FIG. 4).

Therefore, it could be seen that the sustained-release formulation composition including semaglutide of the present invention is a formulation capable of maintaining effects for a long time with only a single administration.

Experimental Example 3: Pharmacokinetic Profile of Sustained-Release Microspheres According to Semaglutide Content in Rats (Formulations of Examples 3, 4 and 6)

Microspheres containing semaglutide were administered to 8-week-old SD rats, and blood was collected at a regular time interval to evaluate the drug concentration in the blood and to evaluate a release pattern of the drug in the microspheres in the body. Formulations used in the PK experiment were the formulations of Examples 3, 4 and 6. An amount of drug (semaglutide) administered to the rats was the same 4 mpk regardless of the formulations.

After subcutaneous (SC) injection of formulations of Examples 3, 4 and 6 to 8-week-old male SD rats, a semaglutide concentration in the blood was observed over time. At 1 hour, 3 hours, 6 hours, 24 hours, or on the $3^{rd}$ day, the $5^{th}$ day, the $7^{th}$ day, the $9^{th}$ day, the $11^{st}$ day, the $14^{th}$ day, the $16^{th}$ day, the $18^{th}$ day, the $21^{st}$ day, the $24^{th}$ day, the $28^{th}$ day, the $31^{st}$ day and the $35^{th}$ day after injection, 0.5 ml of blood was collected from the jugular vein and stored at −80° C. Thereafter, LC-MS/MS analysis was performed.

Figure 5:
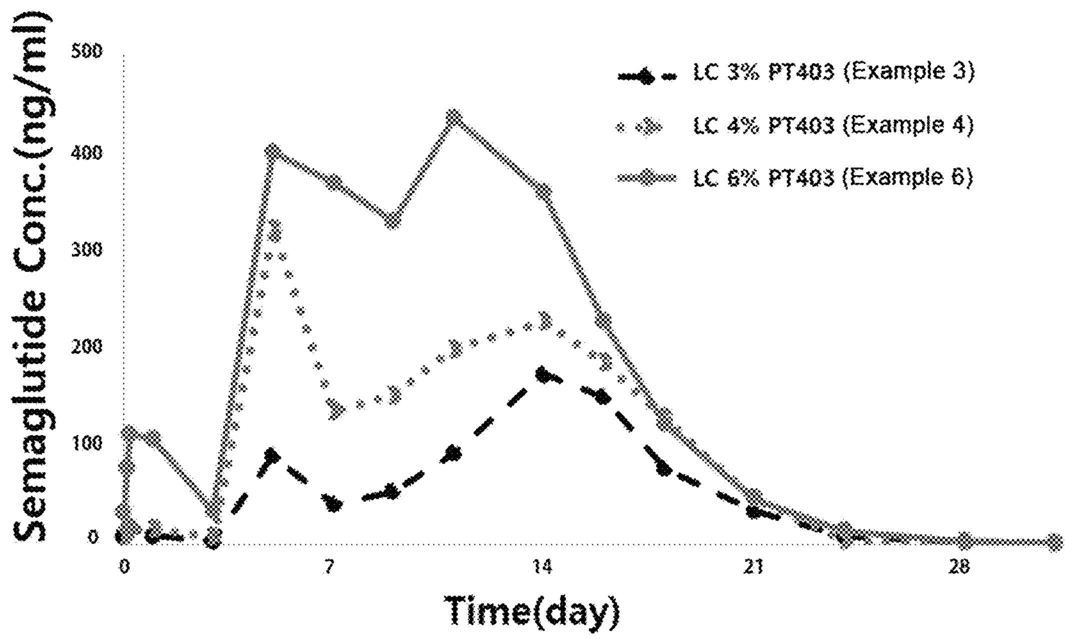
FIG. 5 illustrates drug concentrations in the blood over time after administration of the formulations in Examples 3, 4 and 6, having semaglutide contents (Loading Capacity, LC) of 3, 4 and 6% by weight ("wt. %"), respectively, at the same dose of 4 mpk to male 8-week-old SD rats.

A relative bioavailability was compared by calculating the area under the curve (AUC) from the blood concentration curve over time (FIG. 5). As a result, it was confirmed that the bioavailability was increased as the drug content was increased. In particular, it was confirmed that the microspheres of Example 6, in which the content of semaglutide is 6 wt. %, showed the best bioavailability.

Table 7 shows the PK parameters in SD rats of Examples 3, 4 and 6, while Table 8 shows the cumulative release rate of semaglutide.

TABLE 7

| PK parameter | Example 3 | Example 4 | Example 6 |
|---|---|---|---|
| Initialburst (ng/ml) | 15.22 ± 6.14 | 16.69 ± 4.32 | 117.00 ± 18.87 |
| InitialTime (hour) | 6.00 ± 0.00 | 9.60 ± 8.05 | 13.20 ± 9.86 |
| $C_{max}$ (ng/ml) | 175.30 ± 47.53 | 321.42 ± 148.15 | 503.76 ± 144.26 |
| $T_{max}$ (day) | 14.40 ± 0.89 | 5.00 ± 0.00 | 8.60 ± 3.29 |
| $AUC_{last}$ (ng*day/ml) | 1645.53 ± 423.62 | 3074.21 ± 988.85 | 5320.62 ± 1206.39 |
| $AUC_{3\text{-}28\ d}$ (ng*day/ml) | 1621.11 ± 419.66 | 3038.06 ± 984.46 | 5080.06 ± 1164.19 |

TABLE 8

| Cumulative release (%) | Example 3 | Example 4 | Example 6 |
|---|---|---|---|
| 1 day | 0.58 | 0.52 | 2.01 |
| 7 days | 16.74 | 29.84 | 33.29 |
| 14 days | 65.89 | 76.04 | 83.25 |
| 21 days | 97.86 | 99.43 | 99.03 |
| 28 days | 99.92 | 99.98 | 99.97 |

Experimental Example 4: Pharmacodynamic Profile of Sustained-Release Microspheres Including Semaglutide in Beagles (Formulation of Example 3)

Following the rats, as the formulation used for PK experiments in Beagle dogs, the formulation of Example 3 was used. Further, an amount of the administered drug was 4 mpk which was the same in Experimental Example 3.

After subcutaneous (SC) injection of the formulation of Example 3 to a male Beagle, a semaglutide concentration in the blood was observed over time. At 1 hour, 3 hours, 6 hours, 24 hours, or on the $3^{rd}$ day, the $5^{th}$ day, the $7^{th}$ day, the $9^{th}$ day, the $11^{st}$ day, the $14^{th}$ day, the $16^{th}$ day, the $18^{th}$ day, the $21^{st}$ day, the $23^{rd}$ day, the $25^{th}$ day, the $28^{th}$ day, the $31^{st}$ day, the $35^{th}$ day, the $38^{th}$ day, the $42^{nd}$ day, the $45^{th}$ day, the $49^{th}$ day, the $56^{th}$ day, the $63^{rd}$ day and the $70^{th}$ day after injection, 1 ml of blood was collected from the jugular vein and stored at −80° C. Thereafter, LC-MS/MS analysis was performed.

Figure 7:
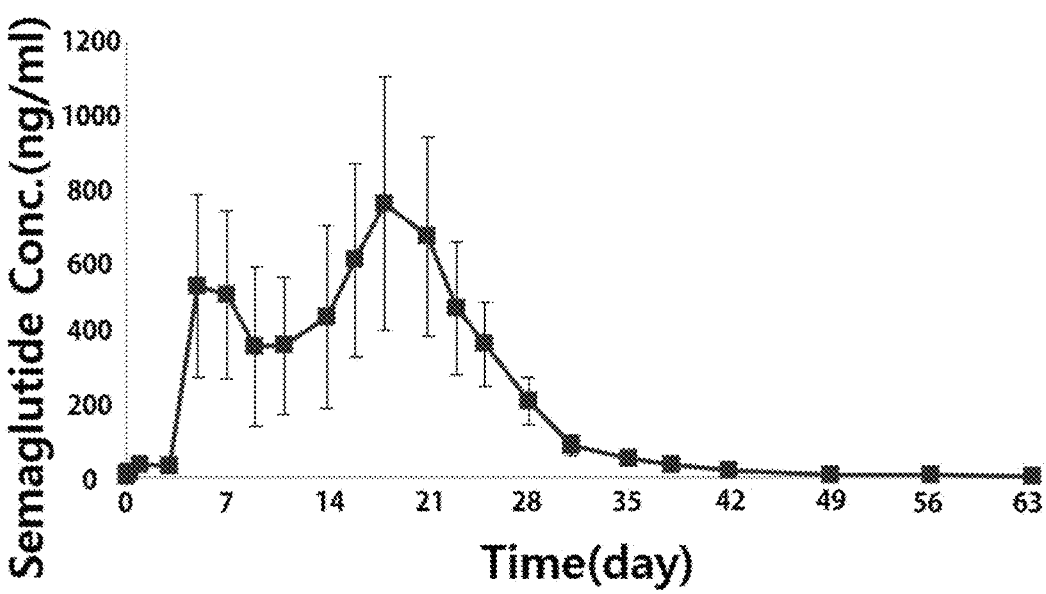
FIG. 7 illustrates drug concentrations in the blood over time after administration of the formulation in Example 3 at a dose of 4 mpk to a male Beagle.

A relative bioavailability was compared by calculating the area under the curve (AUC) from the blood concentration curve over time (FIG. 7). Further, it was confirmed in the Beagle dogs that the release duration of semaglutide was more extended, as compared to SD rats.

Table 9 shows the PK parameters in Beagle dogs in regard to the formulation of Example 3, while Table 10 shows the cumulative release rate of semaglutide.

TABLE 9

| PK parameter | Example 3 |
|---|---|
| Initialburst (ng/ml) | 32.91 ± 11.71 |
| InitialTime (day) | 1.40 ± 0.89 |
| $C_{max}$ (ng/ml) | 784.07 ± 327.44 |
| $T_{max}$ (day) | 13.40 ± 7.77 |
| $AUC_{last}$ (ng*day/ml) | 12671.82 ± 4336.49 |

TABLE 10

| Cumulative release (%) | Example 3 |
|---|---|
| 1 day | 0.22 |
| 7 days | 17.13 |
| 14 days | 38.69 |
| 21 days | 75.62 |
| 28 days | 94.61 |

Experimental Example 5: Pharmacodynamic Profile of Sustained-Release Microspheres Including Liraglutide in Rats The same procedures as in Experimental Example 3 were performed, except that, instead of the formulation of Example 3 containing semaglutide, the formulations of Comparative Examples 13 and 14 containing liraglutide were subcutaneously (SC) injected to the rats, followed by observing the liraglutide concentration in the blood over time.

Table 11 shows components of the formulations of Comparative Examples 13 and 14.

TABLE 11

| | | Type of biodegradable polymers and mixing ratio | | | |
|---|---|---|---|---|---|
| Division | Active ingredient | Polymer type (1) | Polymer type (2) | (1):(2) mixing ratio | Drug loading (%(w/w)) |
| Comparative Example 13 | Liraglutide | PLGA50A | PLGA50B | 1:2 | 5 |
| Comparative Example 14 | Liraglutide | PLGA50A | PLGA50B | 1:1 | 5 |

Figure 9:
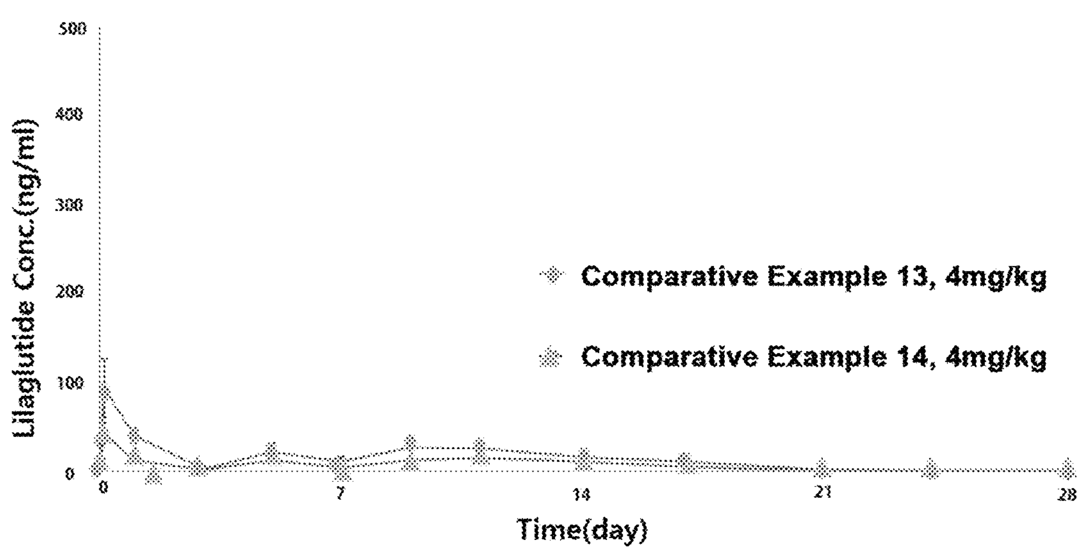
FIG. 9 illustrates drug concentrations in the blood over time after administration of microspheres of formulations in Comparative Examples 13 and 14, each containing liraglutide as an active ingredient, respectively, at the same dose of 4 mpk to male 8-week-old rats.

At 1 hour, 3 hours, 24 hours, or on the $3^{rd}$ day, the $5^{th}$ day, the $7^{th}$ day, the $9^{th}$ day, the $11^{st}$ day, the $14^{th}$ day, the $17^{th}$ day, the $21^{st}$ day, the $24^{th}$ day and the $28^{th}$ day after injection, 0.5 ml of blood was collected from the jugular vein and stored at −80° C. Thereafter, LC-MS/MS analysis was performed to compare the relative bioavailability by calculating the area under the curve (AUC) from the blood concentration curve over time (FIG. 9).

As a result, although liraglutide is a peptide of the same GLP-1 RA family with a structure similar to semaglutide of the present invention, drug release itself was observed to be very little. Through this, it can be seen that it is difficult to predict what type of effects will be exhibited when the type of peptide contained is different even if the biodegradable polymer is used under the same conditions.

REFERENCE TO AN ELECTRONIC SEQUENCE LISTING

A sequence listing electronically submitted with the present application on Nov. 29, 2023 as an ASCII text file name 20231129_LC0672319_TU_SEQ. TXT, created on Nov. 27, 2023 and having a size of 582 bytes, is incorporated herein by reference in its entirety.

What is claimed is:

1. A sustained-release formulation composition, comprising: sustained-release microspheres which include semaglutide or a pharmaceutically acceptable salt thereof, and poly(lactide-co-glycolide);

wherein the semaglutide or the pharmaceutically acceptable salt thereof is included in an amount of 3% by weight to 9% by weight of the sustained-release microspheres, and wherein the poly(lactide-co-glycolide) is a mixture of low-viscosity PLGA having an intrinsic viscosity of 0.14 to 0.24 dL/g and high-viscosity PLGA having an intrinsic viscosity of 0.32 to 0.44 dL/g.

2. The sustained-release formulation composition according to claim 1, wherein a weight ratio of the low-viscosity PLGA and the high-viscosity PLGA in the mixture is 1:0.2 to 5.

3. The sustained-release formulation composition according to claim 1, wherein a molar ratio of lactide to glycolide in the high-viscosity PLGA is 75:25 to 50:50.

4. The sustained-release formulation composition according to claim 1, wherein the sustained-release microspheres are prepared by dissolving the semaglutide or the pharmaceutically acceptable salt thereof and the poly(lactide-co-glycolide) in glacial acetic acid and spraying the same using an ultrasonic spray nozzle, followed by volatilizing the solvent using dry air.

5. The sustained-release formulation composition according to claim 4, wherein the ultrasonic spray nozzle has a frequency of 60 KHz.

6. The sustained-release formulation composition according to claim 1, wherein less than 5% of the semaglutide is released within 24 hours after administration to SD rats, and 30% or more is released within 2 weeks, or 60% or more is released within 4 weeks.

7. The sustained-release formulation composition according to claim 1, wherein the composition is administered to a subject at an interval of 1 to 3 months.

8. The sustained-release formulation composition according to claim 1, wherein the poly(lactide-co-glycolide) is 91 to 97% by weight of the sustained-release microspheres.

9. The sustained-release formulation composition according to claim 1, wherein the sustained-release microspheres have an average particle size of 15 to 25 μm.

10. The sustained-release formulation composition according to claim 1, wherein the composition is used for treatment of diabetes, obesity or non-alcoholic steatohepatitis.

11. A method for production of a sustained-release formulation composition, the method comprising:

preparing a mixed solution by dissolving semaglutide or a pharmaceutically acceptable salt thereof and poly (lactide-co-glycolide) in an organic solvent; and drying the mixed solution to obtain microspheres, wherein the poly(lactide-co-glycolide) is a mixture of low-viscosity PLGA having an intrinsic viscosity of 0.14 to 0.24 dL/g and high-viscosity PLGA having an intrinsic viscosity of 0.32 to 0.44 dL/g.

12. The method according to claim 11, wherein a weight ratio of the low-viscosity PLGA and the high-viscosity PLGA in the mixture is 1:0.2 to 5.

13. The method according to claim 11, wherein a molar ratio of lactide to glycolide in the high-viscosity PLGA is 50:45 to 55.

14. The method according to claim 11, wherein the drying of the mixed solution is performed by a spray drying process.

15. A method for treating diabetes, obesity, non-alcoholic or steatohepatitis, comprising administering the sustained-release formulation composition according to claim 1 to a subject.

* * * * *

SEQUENCE LISTING

<160> NUMBER OF SEQ ID NOS: 1

<210> SEQ ID NO 1
<211> LENGTH: 29
<212> TYPE: PRT
<213> ORGANISM: Homo sapiens

<400> SEQUENCE: 1

His Glu Gly Thr Phe Thr Ser Asp Val Ser Ser Tyr Leu Glu Gly Gln
1 5 10 15

Ala Ala Glu Phe Ile Ala Trp Leu Val Arg Gly Arg Gly
20 25